United States Patent
Urban

Patent Number: 5,676,544
Date of Patent: Oct. 14, 1997

[54] DENTAL TOOL FOR PERIODONTAL CLEANING AND MEASUREMENT OF PERIODONTAL CONDITION

[76] Inventor: Marcia A. Urban, 4700 Kylemore Ct., Palm Harbor, Fla. 34685

[21] Appl. No.: 568,078

[22] Filed: Dec. 6, 1995

[51] Int. Cl.[6] .................... A61C 17/00; A61C 19/04
[52] U.S. Cl. ........................... 433/147; 433/72
[58] Field of Search .................. 433/72, 75, 141, 433/142, 143, 144

[56] References Cited

U.S. PATENT DOCUMENTS

| | | | |
|---|---|---|---|
| D. 331,464 | 12/1992 | Rosenberg et al. | |
| 567,589 | 8/1896 | Fredericks | |
| 575,750 | 1/1897 | Winkler | |
| 1,327,114 | 1/1920 | Rhein | |
| 2,715,899 | 8/1955 | McLean | |
| 3,562,913 | 2/1971 | Saffro | 433/75 |
| 4,364,730 | 12/1982 | Axelsson | |
| 4,552,531 | 11/1985 | Martin | 433/141 X |
| 4,743,198 | 5/1988 | Kennedy | |
| 4,988,295 | 1/1991 | Kline | |
| 5,044,951 | 9/1991 | Sheridan | 433/72 |
| 5,096,420 | 3/1992 | Loewenthal | |
| 5,137,447 | 8/1992 | Hunter | 433/72 |
| 5,169,314 | 12/1992 | Long | |
| 5,178,537 | 1/1993 | Currie | |
| 5,188,617 | 2/1993 | Linder | 433/72 X |
| 5,217,024 | 6/1993 | Dorsey et al. | |
| 5,244,390 | 9/1993 | Lazzara et al. | |

*Primary Examiner*—Nicholas D. Lucchesi
*Attorney, Agent, or Firm*—Mayer, Brown & Platt

[57] ABSTRACT

The present invention relates to an instrument for subgingival scaling, root planing and maintenance of periodontal health. The instrument has an elongated body with a handle portion, a terminal shank portion, a working end, and a gauge. The terminal shank portion includes a base having a first portion, which is coaxial with the handle portion, and a second portion, which is angled from the first portion. The working end has a rear heel portion adjacent to the second portion and a front toe portion. Between the heel and toe there is a blade edge extending lengthwise. The gauge is arranged along the annular surface of the second portion of the terminal shank. In order to measure the periodontal health of the patient on whom the instrument is being used, the instrument is inserted into the periodontal space between the tooth and the gum. The depth of the periodontal space is determined by reading the marking on the gauge which meets the gumline.

10 Claims, 2 Drawing Sheets

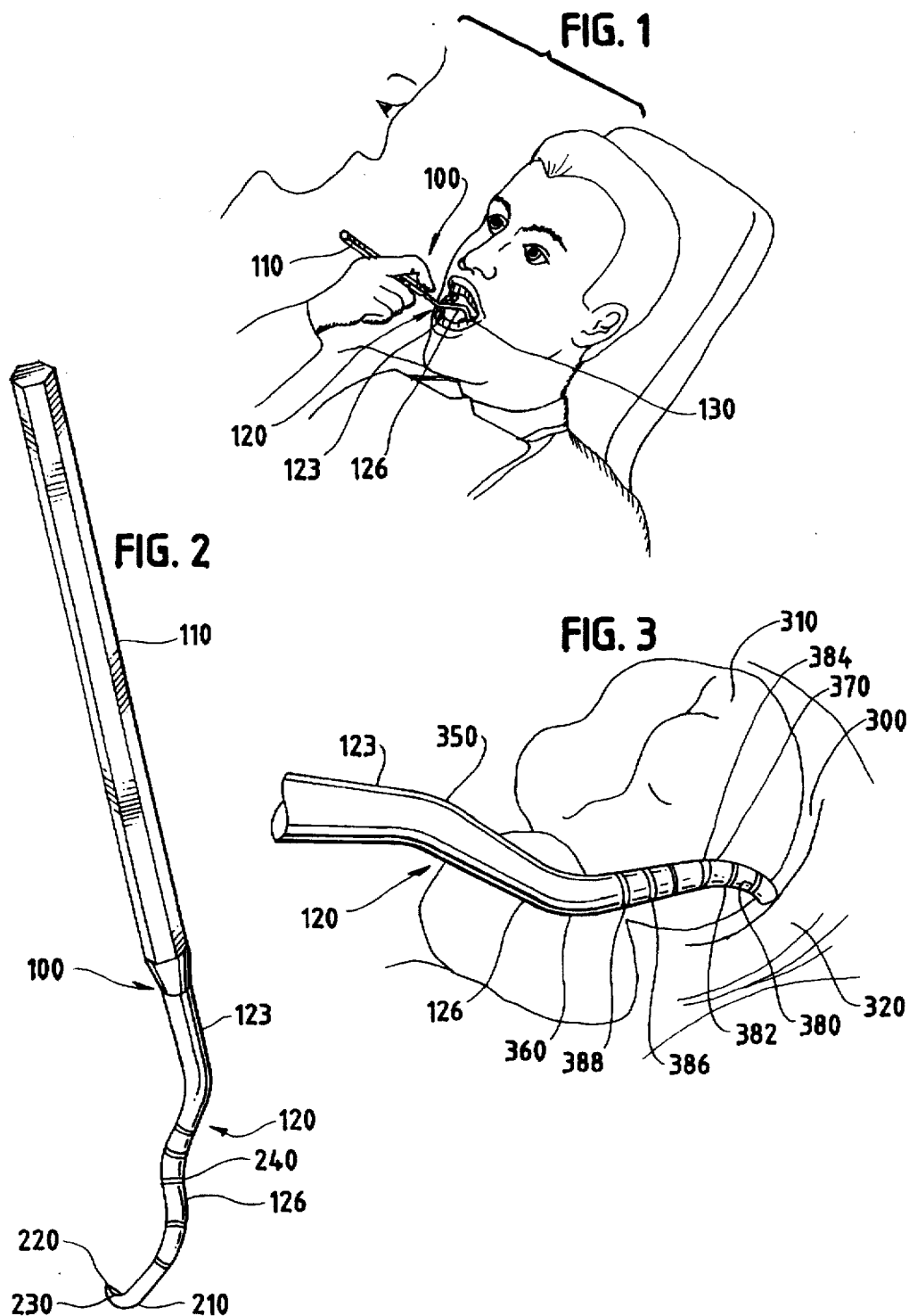

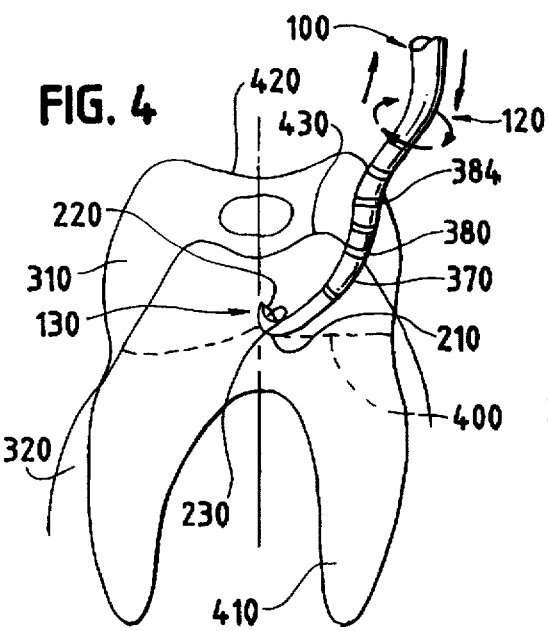
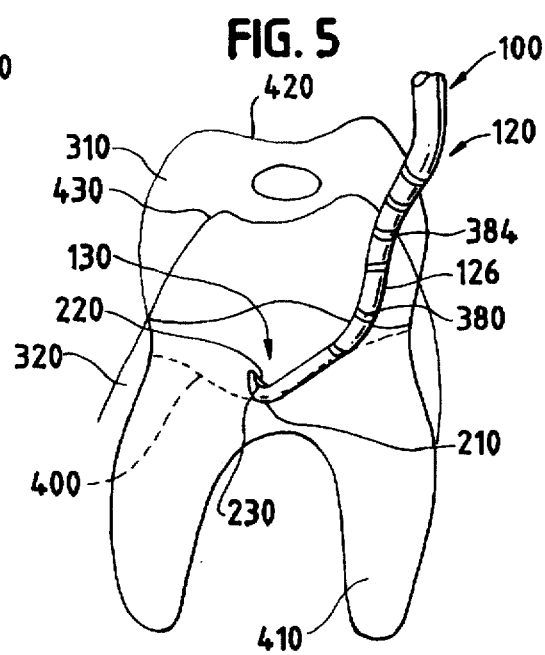
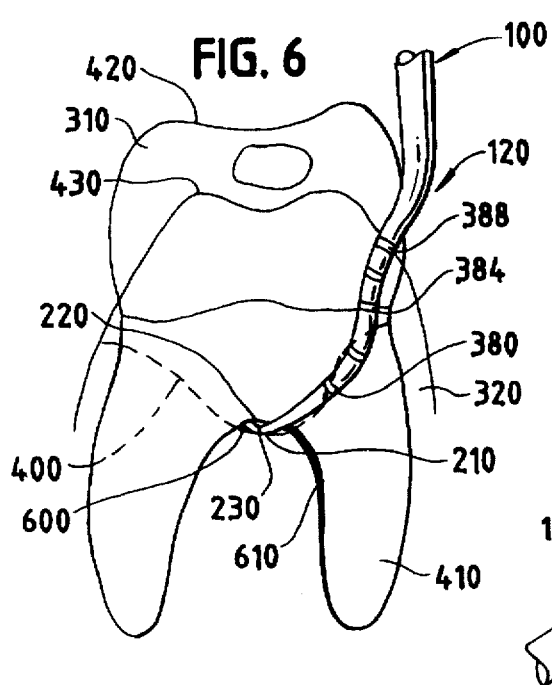
FIG. 7
PRIOR ART
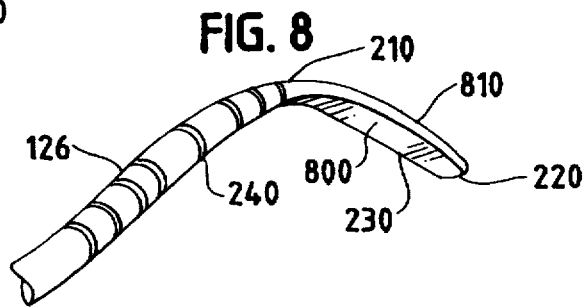
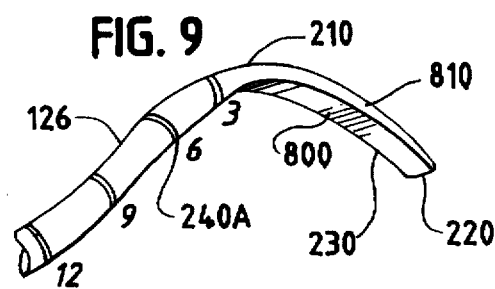
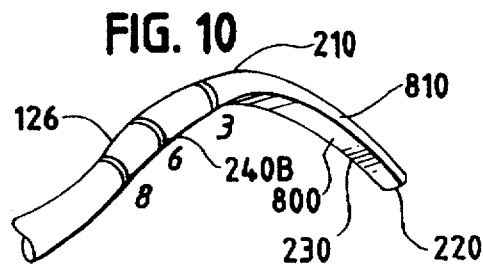

DENTAL TOOL FOR PERIODONTAL CLEANING AND MEASUREMENT OF PERIODONTAL CONDITION

FIELD OF THE INVENTION

The present invention relates to a dental instrument for subgingival scaling, root planing and maintenance of periodontal health, that can not be provided by a periodontal probe alone. Particularly, the present invention is directed to a curette which has been specifically designed in its size and shape for a particular area of the mouth. The curette includes near or on the working end a gauge consisting of annular markings which, when inserted in the space between a tooth and its surrounding tissue, measures the depth of that space and helps to determine the periodontal condition of the patient.

BACKGROUND OF THE INVENTION

With the emphasis of preventive dentistry, fluoride, and good oral hygiene, human teeth are lasting longer and the major concern is no longer decay, but periodontal disease. Periodontics is a branch of dentistry that deals with the diseases of the supporting and investing structures of the teeth including gums, cementum, periodontal membrane and alveolar bone. In order to properly evaluate the periodontal health of a patient, it is necessary to invade the area between the tooth structure itself, and the gum tissue, called the sulcus, to obtain a measurement of this area. This area is where deposits of calculus and plaque are found on the tooth below the gumline. This is also the area where periodontal disease begins. Two of the many instruments used to invade this area for periodontal work are the probe and the curette.

Traditionally, periodontal probes to assist in the treatment of a patient have been used to establish the periodontal condition of a patient, including determining whether bone loss has occurred and the existence and extent of any infection. Probes also serve as guides for instrumentation, to determine root configuration and irregularities that may complicate instrumentation. Probes are calibrated in millimeters (mm) and there are many different types that can be used. A healthy reading of the depth of the periodontal space would be from 1-3 mm, and any measurement over 3 millimeters would be an area of periodontal concern.

In the past, the periodontal probe was the only accurate way to locate and measure periodontal pockets. The probe includes an elongated body that acts as a handle and a generally elongated conical working end oriented normally to the body. The probe is used by gently inserting the working end under the gumline, and with a light grasp, "walking" it around the tooth, never losing contact, to obtain a measurement. For an accurate measurement, the working end must remain parallel with the long axis (an imaginary line that passes through the center of the tooth) of the tooth. Remaining parallel to the long axis can be difficult on posterior teeth, or molars, since they are multi-rooted. When two teeth are contacting, it becomes impossible to remain parallel to the long axis at the point of contact, because the probe will not fit in the area between the teeth.

On molars, when bone has been destroyed by disease between the roots, this leaves an area called a furcation. On maxillary, or upper teeth, the furcations are only accessible from the direct mesial, distal and buccal of the tooth (front, back, and cheek side) and when there are other teeth in contact, an accurate measurement is not possible. Even more distressing is the fact that most periodontal problems occur interproximally, or between the teeth in this area. Unfortunately, measurements in these areas are compromised because probes can not be used as efficiently.

Although probes are used to measure and map the size of periodontal pockets around the teeth, probes do not have the blade edge found on a curette. The blade of the curette is used for removing calculus and altered cementum to produce a smooth tooth surface. The curette is one of the primary instruments that is used for subgingival scaling and root planing. Curettes are the most widely used of all hand scalers because they are area specific. Posterior curettes are configured and formed with angled shanks to provide superior access to the molars. The unique design of curettes allows easy insertion below the gumline with minimal discomfort to the patient. With the curette's sharp cutting edge, the user's tactile sensitivity is magnified, allowing her to better evaluate areas of concern. Curettes offer precision subgingivally which is unobtainable with a probe. When a light grasp or exploratory stroke used with the probe is then used with a curette having a sharp blade, there is more effective feeling of the subgingival area, increased accuracy below the contact due to the angled shanks, and less trauma to the tissue.

In order to remove diseased tissue, calculus and plaque from the subgingival region, curettes are designed with a specific angle of approach for each area of the mouth and each type of tooth. One of the standards in the industry for many years has been the Gracey set of curettes. This set of curettes was designed by Dr. Clayton H. Gracey in the late 1930s. The curettes of this set have one cutting edge and are designed for use in specific areas of the mouth making them particularly suitable for subgingival scaling and root planing of periodontal patients. The objective of Gracey curettes is to be able to reach into pockets where access is difficult in a manner to properly remove calculus and plaque with minimal tissue trauma.

A set of Gracey curettes can be made up of several different instruments, with each instrument being specifically designed to adapt effectively in a certain area of a person's oral cavity. The more bends and angles in the shank, the further posterior it is to be used. The numerical designation of the Gracey instruments and the areas of their use are as follows: Gracey 1–2 (Anterior teeth); Gracey 3–4 (Anterior teeth); Gracey 5–6 (Anterior and bicuspid teeth); Gracey 7–8 (Anterior and bicuspid teeth); Gracey 9–10 (Posterior teeth-buccal and lingual surfaces); Gracey 11–12 (Posterior teeth-mesial surfaces); Gracey 13–14 (Posterior teeth-distal surfaces); Gracey 15–16 (Posterior teeth-mesial aspect); and Gracey 17–18 (Molars-distal surfaces).

With the present invention, accurate measurement will be available in places where measurements before were compromised or even unobtainable. With the present invention configured for specific areas, and calibrating the shank, we can now obtain extremely accurate readings in areas where the probe has never gone before. For example, in a patient with periodontal problems, heavy subgingival deposits, and deep pockets, along with current dental films, and current probings, the exact site of a deposit can be identified. With a calibrated shank on a curette, the hygienist can be assured of the location and depth of the instrument to insure removal of the deposit. After the deposit has been removed and the area thoroughly root planed, the curette can also be used to obtain a new probing depth without switching instruments. Also with a calibrated shank on a curette, when scaling a furcation, the blade is able to adapt to the root surface throughout the entire area and an accurate measurement can be obtained. On the other hand, if a probe were to be used, the measurement would be less precise because the probe must be held at varying angles to stay in contact with the root surface in a furcation. Teeth are three dimensional, and furcations are complex, making it difficult to use a probe in these areas, because the design of the probe requires it to be held parallel to the tooth. Moreover, because the hygienist can not physically see under the gumline, the hygienist uses the instrument and a knowledge of the tooth's anatomy to know location within the periodontal space. With a sharp blade, tactile sensitivity is increased, helping the hygienist to "see" better and more accurately determine how an area is shaped.

DESCRIPTION OF RELATED ART

In the prior art, dental and medical instruments designed to measure tissue depth have been used. However, these instruments require manual adjustment to provide an instantaneous measurement of tissue depth. For example, U.S. Pat. No. 5,217,024 issued to Dorsey et al., teaches a medical device for removing tissue, such as endometrial tissue, from a body cavity, such as the human uterus. The device includes an indicator to allow the user to know how the cutting edge is oriented within the body at all times and the cutting edge has an embossed scale for measuring the depth of insertion. The scale is used to measure the distance into the cavity that the device has been inserted, it does not measure the space between tissues.

U.S. Pat. No. 1,327,114 issued to Rhein teaches an attachable or permanent depth gauge which is used with dental and medical instruments to for example, measure the length of a root canal. The gauge disclosed has two members, the first member being affixed or attached to the handle of the instrument and the second member being movable with respect to the first. Depth is measured by viewing an indicator which reflects the distance between the second member and the extremity of the instrument. The sliding gauge must be positioned to the zero point before the measurement is taken and the instrument must be removed from the patient's mouth in order to read the scale.

U.S. Pat. No. 4,364,730 issued to Axelsson teaches a periodontal probe having a handle portion and a rotatable pin member. The rotatable pin member has either a straight, flat end portion or a circular end portion. The rotational movement of the pin member allows contact with the side of a tooth at the correct angle for insertion. The flat end portion of the rotatable pin member is taught as being graduated with millimeter divisions for measurement purposes.

U.S. Pat. No. 4,988,295 issued to Kline teaches dental instruments such as curettes having one or more annular rings formed in the handle of the instrument with the number of annular rings and their positioning indicating the appropriate instrument for use in treating the various locations and tooth surfaces within the mouth. One, two or three annular rings or grooves are formed in the peripheral surface of the metallic handle of the instrument. The marking system uses one or two rings to indicate the section of the mouth which can be treated with the angle of the particular tool; three rings indicates a special blade; the distance of the rings from the designated end of the handle indicates whether distal or mesial tooth surfaces should be treated. Further spacing of the rings relative to the end of the handle indicates the size of the tooth surface to be treated.

In view of the above, there remains a demand for a dental instrument having a working end with a blade on the lower portion of a shank, such as a curette, with a gauge embossed along the shank surface for measurement of periodontal condition. While the probes of the prior art have been calibrated, they do not permit adaptation for accurate measurement of interproximal areas and furcations of the posterior teeth, especially when they contact adjacent teeth. Curettes have angled shanks to improve access and control to these areas. The sharp edge of a curette increases tactile sensitivity for improved evaluation. The precision of curettes allows for a superior feeling of the subgingival area with less trauma to patient's tissues and increased accuracy in the interproximal areas and furcations. The curettes of the prior art have lacked an embossed calibration with which measurements of the periodontal area can be made with the same, as opposed to a separate, manual action normally required to use the tool. One of the primary benefits of the present invention is that it allows accurate readings in areas that before were not possible or that were compromised. Using the invention, a dentist or hygienist can be assured of the location and depth of the instrument at all times to assure removal of the deposit and debridement of the entire area. After the deposit has been removed and the area has been root planed, the invention can also be used to obtain a new probing depth without having to remove the instrument and insert a periodontal probe.

SUMMARY OF THE INVENTION

The purpose and advantages of the invention will be set forth in and apparent from the description and drawings that follow, as well as will be learned by practice of the invention. Additional advantages of the invention will be realized and attained by the elements of the instrument and method particularly pointed out in the appended claims.

To achieve these and other advantages and in accordance with the purpose of the invention, as embodied and broadly described herein, the invention encompasses a dental instrument for subgingival scaling, root planing and maintenance of periodontal health. The instrument has an elongated body with a handle portion, an adjacent terminal shank portion, a working end, and a gauge arranged along the annular surface of the terminal shank. The terminal shank portion has a base with a first portion that is substantially coaxial with the handle portion and a second portion which is angled from the first portion and the handle. The working end has a rear heel and a front toe with a blade edge extending lengthwise from the heel to the toe. There is a gauge embossed on the annular surface of the terminal shank portion of the device.

The objects and advantages of the present invention are further achieved by a method for providing subgingival scaling, root planing and maintenance of periodontal health. The method begins with insertion of the inventive instrument at a juncture between a tooth and the surrounding gum. The distal end of the instrument is examined and the embossed gauge is read to determine the depth of the periodontal space. The instrument is manipulated in and out of the juncture to remove plaque and other obstructions. The steps detailed above may be repeated until the desired area of the patient's mouth is examined.

It is to be understood that both the foregoing general description and the following detailed description are exemplary and provided for purposes of explanation only, and are not restrictive of the invention, as claimed.

BRIEF DESCRIPTION OF THE DRAWINGS

The accompanying drawings, which are incorporated in and constitute a part of this specification, illustrate the preferred embodiment of the invention, and together with the description, serve to explain the principles of the invention.

FIG. 1 is a perspective representation of a dental professional using the present invention on a patient to examine and measure periodontal space.

FIG. 2 is an elevational view of the present invention;

FIG. 3 is a perspective view of the present invention positioned in the space between the tooth and gum as occurs during periodontal examination;

FIG. 4 is a side view of the present invention positioned in the periodontal space, showing a measurement of 3 millimeters on the embossed gauge generally indicating good periodontal condition;

FIG. 5 is a side view of the present invention positioned in the periodontal space, showing a measurement of 5 millimeters on the embossed gauge generally indicating poor periodontal condition;

FIG. 6 is a side view of the present invention positioned in the periodontal space, showing a measurement of 7 millimeters on the embossed gauge generally indicating severely deteriorated periodontal condition;

FIG. 7 is a planar view of a prior art periodontal probe with an embossed gauge indicating distance in millimeters;

FIG. 8 is a planar view of the blade edge and shank portion of the present invention with an embossed gauge indicating distance in millimeters according to the Williams system of calibration;

FIG. 9 is a planar view of the blade edge and shank portion of the present invention with an embossed gauge indicating distance in millimeters according to the CP-12 system of calibration;

FIG. 10 is a planar view of the blade edge and shank portion of the present invention with an embossed gauge indicating distance in millimeters according to the Michigan system of calibration.

DETAILED DESCRIPTION OF THE PREFERRED EMBODIMENT

Reference will now be made in detail to the present preferred embodiment of the instrument and method of obtaining and maintaining periodontal health using the instrument of the invention, examples of which are illustrated in the accompanying drawings. Wherever possible, the same reference characters will be used throughout the drawings to refer to the same or like parts. The method of the present invention will be described in conjunction with the detailed description of the dental instrument for clarification.

The preferred use of the present invention, without limitation, is obtainment and maintenance of periodontal health. The instrument comprises an elongated body having a handle portion, an adjacent terminal shank portion, a working end, and a gauge arranged along the annular surface of the terminal shank portion. The terminal shank portion includes a base which has a first portion that is substantially coaxial with the handle and a second portion that is angled from the first portion. The working end has a rear heel portion which is adjacent to the second portion of the terminal shank and a front toe portion. There is a blade edge on the working end having a lengthwise working axis which extends laterally from the rear heel portion to the front toe portion. The gauge is arranged along the annular surface of the second portion of the terminal shank.

In a preferred embodiment of the invention, the terminal shank and working end portions are of the design known as a Gracey curette, having one blade edge and being sized and shaped for a specific area of the mouth, and the gauge is embossed into the annular surface of the terminal shank.

Preferably, the gauge can be used to measure the depth of periodontal space in millimeters. When the instrument is inserted into the periodontal space, the blade edge of the working end is parallel with the top surface of the tooth. The gauge, which is embossed into the second portion of the terminal shank, indicates the depth of the periodontal space in millimeters when the blade edge is parallel to the top surface of the tooth and the terminal shank portion is held parallel to the longitudinal axis of the tooth.

An exemplary embodiment of the instrument of the present invention is shown in FIG. 1 and designated generally by reference character 100. FIG. 1 illustrates a dental professional utilizing the instrument 100 to determine the periodontal condition of a patient. The instrument 100 has a handle 110 which is manually grasped by the professional, a terminal shank portion 120, and a working end 130. The handle 110 is generally cylindrical and may include ridges or a rough surface to assist the user in grasping the instrument. Alternatively the handle 110 may be hexagonal or octagonal in cross-section. It is preferred that the instrument be made from stainless steel, plastic or other material well known in the art which will not substantially deteriorate from abrasive action against the teeth and bones and which can be cleaned, disinfected and sterilized by well known procedures such as autoclaving, ultraviolet light and the like.

The terminal shank 120 includes a first portion 123 and a second portion 126. The first portion 123 is coaxial with the handle 110 and considerably smaller in diameter than the handle 110. The second portion 126 is integral with and angled from the first portion 123. As can be seen in FIG. 3 the diameter of the shank portion 120 gradually tapers as it approaches the working end 130.

Referring now to FIG. 2, the working end 130 of the instrument 100 is visible. The working end 130 is adjacent to and integral with the second portion 126 of the terminal shank 120. The working end 130 includes a rear heel portion 210 and a front toe portion 220. The working end 130 also includes a blade edge 230 having a lengthwise working axis extending laterally from the rear heel 210 to the front toe 220. A gauge 240 is arranged along the annular surface of the second portion 126. The gauge 240 indicates the depth to which the working end 130 has been inserted when the instrument 100 is being used. The gauge 240 is preferably embossed on the annular surface of the second portion 126. The gauge 240 includes annular markings preferably separated at 1 mm intervals. An exemplary gauge is a Williams calibration where the markings are spaced to indicate depths of 1, 2, 3, 5, 7, 8, 9, and 10 millimeters. There are other calibration schemes which can be used and are known in the art.

FIG. 3 shows a close-up view of the instrument 100 positioned in the periodontal space 300 of a patient. The periodontal space is located between the tooth 310 and the gum 320. The first portion 123 and second portion 126 of the terminal shank 120 are visible in this view. The working end 130 is not visible as it is below the gumline in the periodontal space 300. The second portion 126 is angled from the first portion 123, which is coaxial with the handle 110 (not visible). The second portion 126 has three angles from the first portion 123: a first angle 350, a second angle 360, and a third angle 370. The angles of the second portion 126 allow the professional access to areas of the mouth not reachable with a periodontal probe. The angles are varied as is known in the art depending on the area of the mouth for which the instrument 100 is designed. The gauge 240 is depicted between the third angle 370 and the second angle 360 of the second portion 126. The gauge 240 consists of annular markings 380, 382, 384, 386 and 388 positioned to represent respectively depths of 3 mm, 4 mm, 5 mm, 6 mm, and 7 mm. A reading of the gauge 240 based on the position of the instrument 100 in FIG. 3 shows a periodontal space 300 depth of 3 mm indicating a healthy periodontal condition.

FIGS. 4–6 illustrate side views of the instrument 100 positioned in the periodontal space 300 indicating a spectrum of periodontal health. In FIG. 4 the instrument 100 is positioned in the periodontal space 300 between the tooth 310 and the gum 320. In this side view, the root 410 of the tooth 310 is visible. The depth 400 of the periodontal space 300 is indicated by the broken line across the width of the tooth 310. When the instrument 100 is positioned this way, the shank 120 is parallel to the long axis of the tooth 310 and the working end 130 is perpendicular to the side of the tooth 310. The front toe portion 220 touches the side of the tooth 310 and the rear heel portion 210 is against the gum 320. The blade edge 230 is on the top side of the working end 130. The blade edge 230 is parallel to the top surface 420 of the tooth 310. The gauge 240 is read to determine the distance between the depth 400 of the periodontal space and the gumline 430. The 3 mm mark 380 is at the gumline 430 indicating good periodontal health. The markings of the gauge 240 are embossed into the annular surface of the second portion 126 of the terminal shank 120. As shown, the 3 mm mark 380 is near the first angle 370 of the second portion 126.

FIG. 5 also depicts a side view of a tooth 310. However, the depth 400 of the periodontal space is substantially greater in FIG. 5 than it was in FIG. 4. Because the depth 400 of the periodontal space is greater, a greater section of the second portion 126 of the terminal shank 120 is below the gumline 430. The depth 400 of the periodontal space measures 5 mm as indicated by the 5 mm mark 384 meeting the gumline 430. In Fig. 6, the periodontal health is severely compromised which is indicated by the depth 400 of the periodontal space extending below a furcation 600 of the tooth 310 and extending across the roots 410. The depth 400 of the periodontal space measures 7 mm as indicated by the 7 mm mark (388) meeting the gumline 430. In FIG. 6 the working end 130 of the instrument 100 is against the interior surface 610 of the root 410. The instrument 100 is easily manipulated so that the blade edge 230 can be adapted to the interior surface 610 of the root 410 and the surface of the furcation 600. Adaptation of the blade edge 230 to the interior surface 610 allows the professional to remove calculus and plague. Simultaneous with the working of the blade edge 230, the gauge 240 on the second portion 126 is used to measure the depth 400 of the periodontal space without needing to switch dental tools.

The method of using the present invention for subgingival scaling, root planing, and maintenance of periodontal health is illustrated by FIGS. 4–6. The instrument 100 of the present invention, having a terminal shank portion 120 and a working end 130, is inserted into a patient's mouth and positioned so that the working end 130 is at the juncture between a tooth 310 and the surrounding gum 320. The second portion 126 is examined and the gauge 240 is read to determine the depth 400 of the periodontal space 300. The professional then manipulates the working end 130 of the instrument 100 in and out of the periodontal space 300 as indicated by the arrows to remove plaque and other obstructions.

FIGS. 8–10 show a series of three instruments 100 of the present invention which differ by the type of gauge 240 embossed into the annular surface of the second portion 126 of the terminal shank 120. The gauge 240 depicted in FIG. 8 has a Williams calibration consisting of markings at the distances of 1, 2, 3, 5, 7, 8, 9, and 10 millimeters. Adjacent to the portion of the terminal shank upon which the gauge 240 is embossed is the working end 130 of the instrument 100. Between the rear heel portion 210 and the front toe portion 220 is the blade edge 230. The blade edge 230 has a flat top surface 800 and a semi-circular bottom surface 810. In FIG. 9, the gauge 240A has a CP-12 calibration consisting of markings at the distances of 3, 6, 9, and 12 millimeters. In FIG. 10, the gauge 240B has a Michigan calibration consisting of markings at the distances of 3, 6, and 8 millimeters.

In view of the description above, it is evident that the present invention provides a novel improvement for the maintenance of periodontal health.

Although reference has been made to the use of the present invention for the maintenance of periodontal health for the purpose of explanation, it is understood that alternative uses are intended to be encompassed by this application. It also will be apparent to those skilled in the art that various modifications and variations can be made in the design and construction of the instrument for maintaining periodontal health, as well as in the performance of the method, without departing from the scope or spirit of the invention.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. An instrument for the maintenance of periodontal health comprising:

an elongated body having a handle portion and an adjacent terminal shank portion, said terminal shank portion having an annular surface and including a base having a first portion substantially coaxial with said handle portion, and a second portion angled therefrom, a distal working end having a rear heel portion adjacent said second portion of said base and a front toe portion, said working end having a blade edge portion and a lengthwise working axis extending laterally from the heel of said working end to said toe portion and a gauge arranged along the annular surface of said terminal shank portion.

2. The instrument of claim 1 where said handle portion is adapted to be manually grasped.

3. The instrument of claim 1 wherein said terminal shank portion is sized and shaped for use in conjunction with a specific area of the mouth.

4. The instrument of claim 1 wherein said gauge is disposed beginning on said second portion of said shank portion, continuing proximately along said shank portion, and terminating before the rear heel portion of said working end.

5. The instrument of claim 4 wherein said gauge includes spaced annular markings.

6. The instrument of claim 5 wherein said spaced markings are calibrated to measure distance in millimeters.

7. The instrument of claim 4 wherein said gauge is comprised of annular markings spaced apart from each other so as to be calibrated to a known scale of measuring periodontal distance.

8. The instrument of claim 1 wherein said gauge is embossed into the annular surface of said terminal shank portion.

9. A curette for maintenance of periodontal health comprising: an elongated body having a handle portion adapted to be manually grasped, an adjacent terminal shank portion, said terminal shank portion having an annular surface and including a base having a first portion substantially coaxial with said handle portion, and a second portion angled therefrom, a distal working end having a rear heel portion adjacent said second portion of said base and a front toe portion, said working end having a blade edge portion and a lengthwise working axis extending laterally from said heel portion of said working end to said toe portion and a gauge embossed into the annular surface of said terminal shank portion being calibrated in millimeters where said gauge begins on the second portion of said shank portion, continues proximately along said shank portion, and terminates before the rear heel portion of said working end.

10. A method for providing subgingival scaling, root planing, and maintenance of periodontal health comprising the steps of:

(a) providing a periodontal curette having an elongated body with a handle portion and an adjacent terminal shank portion, said terminal shank portion having an annular surface and including a base having a first portion substantially coaxial with said handle portion, and a second portion angled therefrom, a distal working end having a rear heel portion adjacent said second portion of said base and a front toe portion, said working end having a blade edge portion and a lengthwise working axis extending laterally from the heel portion of said working end to said toe portion and a gauge arranged along the annular surface of said terminal shank portion;

(b) inserting said working end of said curette at a juncture between a tooth and surrounding gum;

(c) examining the distal end of said curette and reading said gauge to determine the depth of the periodontal space;

(d) manipulating the working end of said curette in and out of said juncture to remove plaque and other obstructions.

* * * * *